(12) United States Patent
Coburn et al.

(10) Patent No.: US 6,407,288 B1
(45) Date of Patent: Jun. 18, 2002

(54) NAPHTHYLSALICYLANILIDES AS ANTIMICROBIAL AND ANTIINFLAMMATORY AGENTS

(75) Inventors: Robert A. Coburn, Williamsville; Richard T. Evans, East Amherst; Robert J. Genco, Snyder, all of NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/969,071

(22) Filed: Oct. 2, 2001

Related U.S. Application Data

(60) Provisional application No. 60/237,319, filed on Oct. 2, 2000.

(51) Int. Cl.[7] .................... C07C 233/65; A61K 31/165
(52) U.S. Cl. .................... 564/169; 514/522; 514/621; 558/415
(58) Field of Search .................... 564/169; 558/415; 514/621, 522

(56) References Cited

U.S. PATENT DOCUMENTS

| | | | | |
|---|---|---|---|---|
| 4,287,191 A | * | 9/1981 | Coburn et al. | 564/169 |
| 4,358,443 A | * | 11/1982 | Coburn et al. | 564/169 |
| 4,742,083 A | * | 5/1988 | Ritchey | 514/617 |
| 4,939,132 A | * | 7/1990 | Coburn et al. | 514/166 |
| 5,958,911 A | * | 9/1999 | Evans et al. | 514/166 |

* cited by examiner

*Primary Examiner*—Shailendra Kumar
(74) *Attorney, Agent, or Firm*—Hodgson Russ LLP

(57) ABSTRACT

The present invention discloses novel naphthylsalicylanilides of the general formula

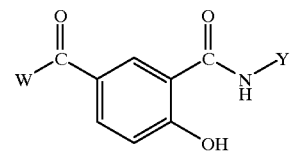

wherein W is a substituted or unsubstituted naphthyl ring. The substitution on W includes replacing one or more —H with —OH, alkyl, O-alkyl, branched alkyl, or cycloalkyl, containing 1–6 carbon atoms or combinations thereof. Y is a substituted or unsubstituted phenyl ring or substituted or unsubstituted naphthyl ring. The substitution for Y includes replacement of one or more —H atoms with CN, $CF_3$, $NO_2$, methoxy, benzoyl, phenoxy, phenoxymethyl or combinations thereof. These compounds are useful as antibacterial against gram negative and gram positive bacteria and as antiinflammatory agents.

27 Claims, 1 Drawing Sheet

NAPHTHYLSALICYLANILIDES AS ANTIMICROBIAL AND ANTIINFLAMMATORY AGENTS

This application claims priority of U.S. provisional application serial No. 60/237,319, filed on Oct. 2, 2000, the disclosure of which is incorporated herein by reference.

FIELD OF INVENTION

The present invention relates generally to the field of antimicrobial agents. More particularly, the present invention provides novel naphthylsalicylanilides and a method for the use of these compounds as antimicrobial and antiinflammatory agents.

DISCUSSION OF RELATED ART

Several Salicylanilide compounds have been identified as potential antimicrobial agents. Previously, some of these agents have been shown to be effective against microorganisms associated with dental plaques.

U.S. Pat. No. 4,287,191 discloses 5-acylsalicylanilides which are said to be effective antiseptics against a wide range of microorganisms, especially bacteria and the microorganisms prevalent in dental plaque. However, these compounds were not found to be effective against antibiotic resistant bacteria such as *S. mutans*. The general structure of these compounds can be represented by the following formula:

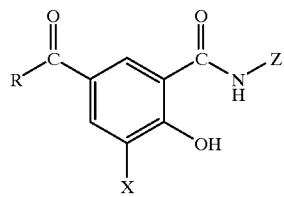

Wherein Z is a substituted phenyl ring, R is a substituted or unsubstituted alkyl or phenyl group and X is —CN, —F, $NO_2$, —H, lower alkyl or lower haloalkyl.

U.S. Pat. No. 4,358,443 discloses 5-alkylsalicylanilides having the same general formula as above wherein R is a substituted or unsubstituted -alkyl or phenyl group.

U.S. Pat. No. 4,939,132 discloses 5-sulfonylalkylsalicylanilides as antimicrobials having the same general formula as above wherein R is a substituted or unsubstituted alkylsulfonyl group.

U.S. Pat. Nos. 4,742,083 and 5,958,911 disclose antiinflammatory effects of salicylanilides.

Given the constant emergence of antibiotic resistant bacteria, there is an ongoing need for novel antimicrobial agents effective against a wide variety of bacteria.

SUMMARY OF THE INVENTION

The present invention provides novel aroylsalicylanilides. In particular, the present invention provides novel 5-naphthylsalicylanilides and describes the antimicrobial effects of these compounds against a wide variety of bacteria. Further, this invention also provides a method of using these compounds for obtaining relief from infections associated with the bacteria.

Accordingly, it is an object of the invention to provide novel naphthylsalicylanilides Another object of the present invention is to provide a method for the use of naphthylsalicylanilides as antimicrobial agents.

A yet another object of the present invention is to provide a method for the control of periodontal disease.

DETAILED DESCRIPTION OF THE INVENTION

Definitions

Figure 1:
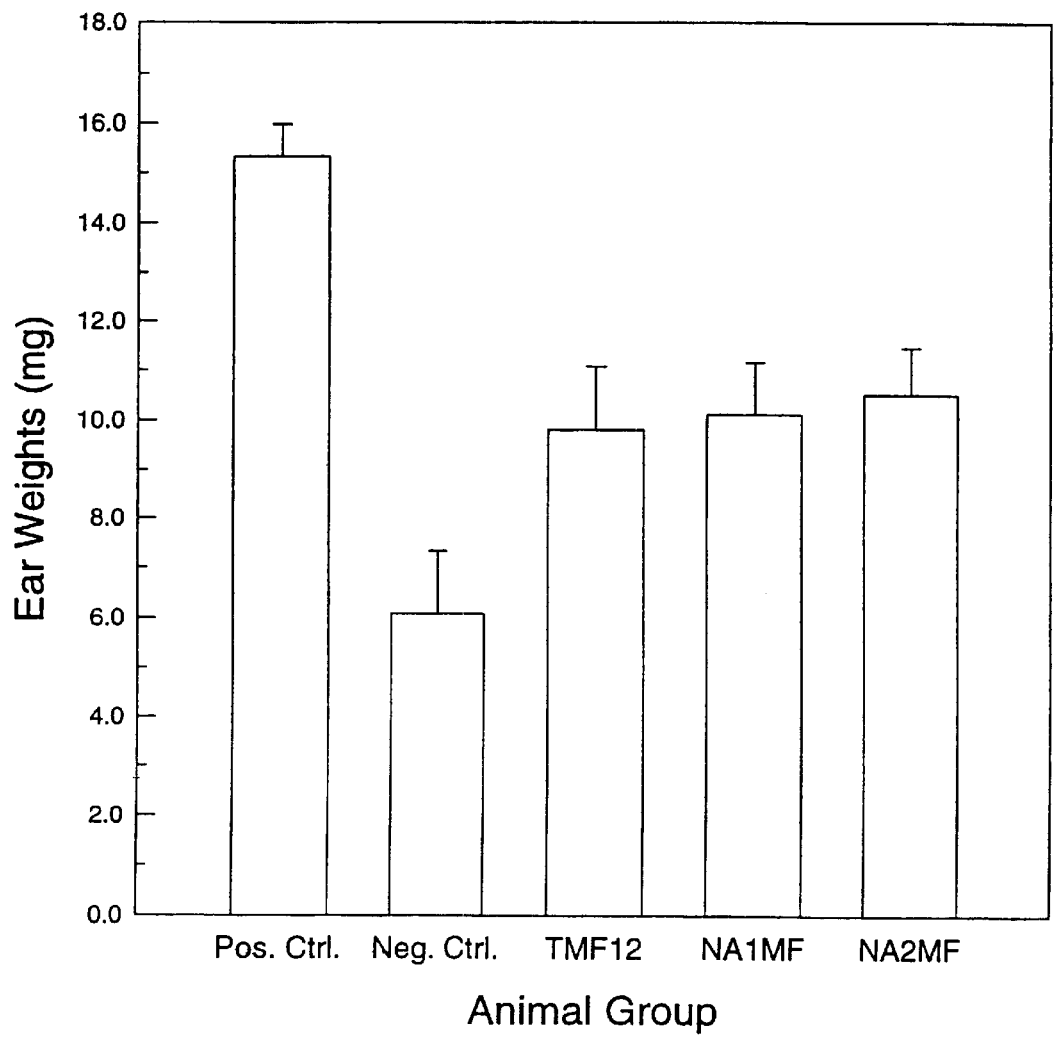
FIG. 1 is a representation of the effect of naphthylsalicylanilides and TMF-12 on the ear weights in a mouse ear inflammation assay.

By the term "partition coefficient" as used herein for the purposes of specification and claims is meant the $\log_{10}P$ where P is the ratio of the molar concentrations of the compositions of the composition in octanol-water system. Partition coefficient is a measure of the lipophilic character of the compound. A partition coefficient of 4 therefore means that the ratio of the concentration of the composition in octanol to the concentration in water is $10^4$ or 10,000 to 1.

By the term "high lipophilicity" as used herein for the purposes of specification and claims is meant a partition coefficient greater than 4.

By the term "substituted" as used herein for the purposes of specification and claims is meant that one or more hydrogens atoms in the compound is replaced with a carbon and/or nitrogen containing moiety such as, but not limited to, alkyl, O-alkyl, branched alkyl, cycloalkyl (all alkyl groups containing 1–6 carbon atoms), CN, $CF_3$, $NO_2$, methoxy, phenoxy, benzoyl, phenoxymethyl and combinations thereof.

The present invention is based on the unexpected observation that 5-naphthylsalicylanilides were observed to be more effective antibacterial agents than the 5-acyl or 5-alkyl salicylanilides disclosed in U.S. Pat. Nos. 4,287,191 and 4,358,443. The compounds of the present invention are encompassed by the following formula (designated herein as Formula 100).

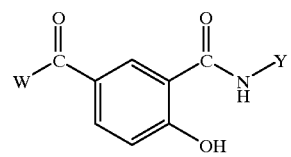

wherein W is a substituted or unsubstituted naphthyl ring. The substitution on W includes replacing one or more —H with —OH, alkyl, O-alkyl, branched alkyl, or cycloalkyl, containing 1–6 carbon atoms or combinations thereof. Y is a substituted or unsubstituted phenyl ring or substituted or unsubstituted naphthyl ring. The substitution for Y includes replacement of one or more —H atoms with CN, $CF_3$, $NO_2$, methoxy, benzoyl, phenoxy, phenoxymethyl or combinations thereof.

In one embodiment, wherein Y is substituted or unsubstituted phenyl group, and W is unsubstituted naphthyl group, the compounds of the present invention may be represented by the following formula (Formula 110):

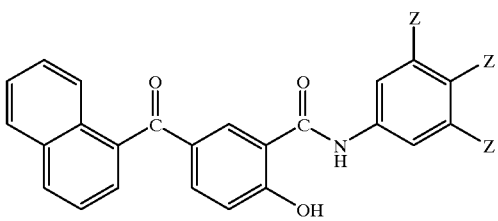

Wherein Z represents the substitution on the phenyl ring. Z is preferably an electron withdrawing group and desirably is not strongly hydrophilic or water solublizing. In one embodiment, Z is independently at each location —H, $CF_3$, —CN or —$NO_2$. When Z is H at each position, the compound is designated herein as NA1. When Z is —$CF_3$ at the meta position, the compound has the following structure:

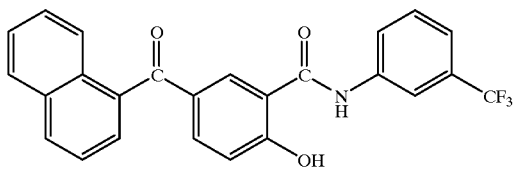

The above compound is referred to herein as NA1mF. This is an α isomer (attachment at the naphthalene 1-position). The β isomer (attachment at the naphthalene 2-position) of this compound is referred to herein as NA2mF. When Z is a —CN group at the meta position, the compound has the following structure.

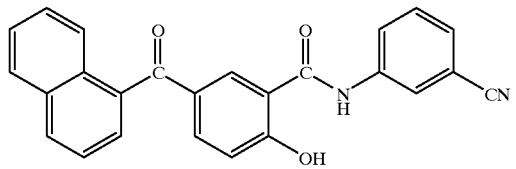

This compound is designated herein as NA1mC(α isomer; attachment at the naphthalene 1-position) or Na2mC (β isomer; attachment at the naphthalene 2-position). When the —CN group is at the para position, the compound is referred to herein as NA1pC (α isomer) or NA2pC (β isomer). Similar isomers for other compounds of the present invention are intended to be within the scope of this invention.

In another embodiment, Z may be a methoxy, phenoxy, benzoyl or phenoxymethyl group. An example when Z is a phenoxymethyl group is as follows.

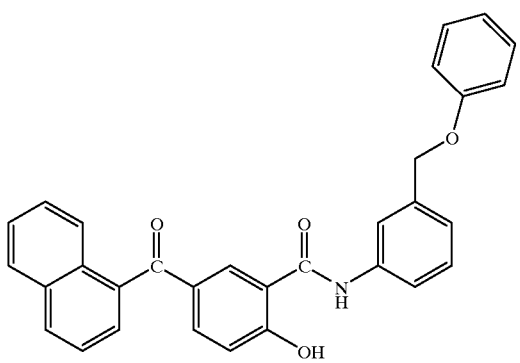

This compound is referred to herein as NA1_3BnOPh.

In another embodiment, the Z substitution is at both the meta positions. An example of a disubstituted compound is as follows, designated herein as NA1mF2.

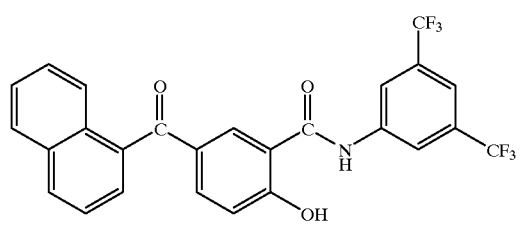

In another embodiment, Y is an unsubstituted or substituted naphthyl ring. An example of a compound when Y is a substituted naphthyl ring is as follows (designated as NA1NpC).

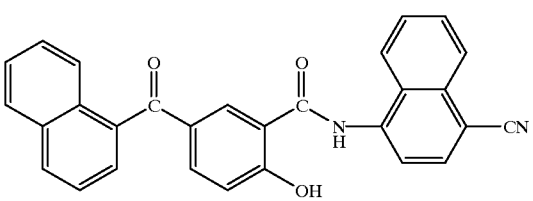

In another embodiment, the naphthyl group W of the naphthylsalicylanilides of Formula 100 may substituted. An example of such a substitution is wherein a —H is substituted by —OH.

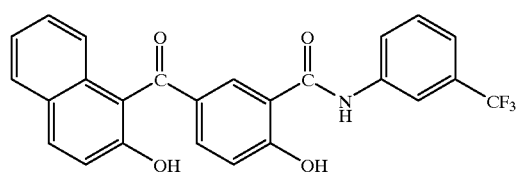

This compound is referred to herein as NA1OHmF.

The compounds of the present invention can be synthesized by a two-step process where the first step prepares the ester to be used for all similar (such as 1-naphthoyl) derivatives with the same aroyl group. In the second step the desired anilide is prepared by reacting the ester with the aniline or aniline derivative.

An advantage of the compounds of the present invention is that they have unexpectedly higher potency than the salicylanilides described previously (U.S. Pat. Nos. 4,287,191; 4,358,443 and 4,939,132). In the compounds of the present invention, the 5-naphthyl groups are connected to the salicylanilides via a carbonyl group.

The introduction of the naphthyl group at the 5-position renders them effective against a wide range of bacteria. Thus, the compounds of the present invention have been found to be effective against both gram positive and gram negative bacteria. These gram positive bacteria include, but are not limited to, *Streptococcus mutans, Streptococcus sanguis, Micrococcus luteus, Streptococcus salivarius, Propionibacterium acnes, Actinomyces viscosus, Staphlococcus aureus, Lactobacillus rhamnosus* (*casei*) 7469. The gram negative bacteria include, but are not limited to, Salmonella, *Fusobacterium nucleatum* 25586, *Actinobacillus actinomycetemcomitans* (Aa) Y4, *Escherichia coli, Porphyromonas gingivalis, Salmonella cholerasuis* (*Sal. chsuis*), *Bacteroides fraglis* and Citrobacter.

Since these compounds are highly lipophilic, they are insoluble in $H_2O$. However, and quite unexpectedly, these compounds were found to be soluble in aqueous solutions of both anionic and non-ionic detergents at concentrations routinely used in topical applications. This property of these compounds makes them suitable as topical antimicrobial and antiinflammatory agents.

Accordingly, the compounds of this invention may be incorporated into formulations for topical application. Such applications include, but are not limited to, topical formulations the treatment of infection of mouth, skin, scalp, ear, nose, eyes, vagina and rectum. The infections treated by these compounds includes various disorders including gingivitis and acne.

The compounds of this invention may also be used as topical antimicrobial or antiinflammatory agents for veterinary use for the relief of infections in various conditions including gingivitis, conjunctivitis and arthritis. The formulations can be applied to, without limitation, mouth, skin, scalp, ear, nose, eyes, vagina and rectum.

The method in accordance with the present invention for the relief of infection or inflammation comprises contacting the affected area with the compounds of this invention in a pharmaceutically acceptable carrier containing alcohols, nonionic or ionic detergent. Such a carrier base may be selected from the group consisting of petroleum jelly, lanolin, paraffin wax, alkanols and mixtures thereof. By using a base such as lanolin or petroleum jelly, a spreadable formulation is obtained and by using a base such as paraffin wax, a stick for topical application is obtained. In addition, the compounds of this invention may also be incorporated into liquid carriers containing alcohols, non-ionic or ionic detergents. Thus, ethanol, the non-ionic detergent, Tween 80™ and the anionic detergent, sodium lauryl sulfate (SLS) may be used.

The above compounds can be used as antimicrobial or antiinflammatory agents in mammals, particularly humans, by topical application of formulations containing the compounds of the present invention. These compounds can be used, without limitation, in tooth pastes, mouth rinses, soaps, shampoos, skin ointments, skin lotions, eye ointments, eye drops, ear drops, and nasal drops.

In addition to the effect of the present compounds on the bacteria associated with dental plaques, another unexpected observation is that these compounds were also found to be effective against bacteria other than those associated with the oral cavity. Accordingly, the drug formulations of the present invention can be used for relief of systemic infections. Thus, these compounds can be used with pharmaceutical carriers suitable for delivery of lipophilic drugs such as, but not limited to, liposomal formulations or aerosols.

Liposomes are phospholipid vesicles which form closed fluid filled spheres when dispersed in aqueous solutions. Phopholipid molecules are polar molecules having a hydrophilic head toward the aqueous side and two hydrophobic tails made of fatty acid chains. At sufficient concentrations, the phospholipid molecules organize into micells with polar heads point toward the aqueous medium and the fatty acid chains point toward the interior of the micelle. Various types of liposomal preparation techniques are described in U.S. Pat. No. 5,958,449, the disclosure of which is incorporated herein by reference. Liposomes may be delivered via routes such as intravenous, subcutaneous and topical. The liposomes may also be directed to target areas with the use of specific targeting agents such as by incorporating specific recognition molecules in the liposomes.

Another method of delivery of the formulations of compounds of the present invention, including liposomal formulations, is via aerosols. Appropriate concentrations for any particular mode of delivery and application will vary with the condition being treated. Determination of such concentrations are well within the purview of one skilled in the art.

The following examples illustrate the invention.

EXAMPLE 1

This example illustrates the synthesis of 2-Hydroxy-5-(naphthalene-1-carbonyl)-N-phenyl-benzamide designated herein as NA1 in a two-step process.

Synthesis of 2-Hydroxy-5-(naphthalene-1-carbonyl)-benzoic acid phenyl ester

The reaction vessel was a 500 ml three neck round bottom pyrex flask fitted with a 250 mL addition funnel, thermometer, a reflux condenser, and a stirrer. Aluminum chloride (7.98 g, 59.8 mmole) and 225 mL of chloroform were added into the round bottom flask and then this stirred suspension was cooled to 5° C. with an external ice-bath. Phenyl salicylate (5.83 g, 27.2 mmole) and naphthalene-1-carbonyl chloride (4.91 mL, 6.21 g, 32.6 mmole) were combined together with 130 mL of chloroform and added dropwise over a hour and half to the stirred suspension. Upon this addition color changes were observed from colorless to light yellow then dark green and finally to dark brown. The temperature was maintained at 5–15° C. during the addition period. Following the addition the reaction mixture was heated to reflux for 48 hours and then allowed to stand at 22° C. for eight hours.

The reaction mixture was slowly added to a stirred slurry of 50 mL of crushed ice to which 125 mL of 12N HCl had been added. The organic layer was isolated in a 1-liter separatory funnel and was washed 5 times with distilled water. Purity was checked on TLC (silica gel plate) and the solvent used was 1:1 ratio of $CH_2Cl_2$ and hexane. Three spots were observed on TLC, the phenyl ester was on the top and the product spot was in the middle.

Purification was achieved by using flash column chromatography on silica gel with the same solvent system described above. There resulted 3.75 g (31%) of the desired product phenyl ester as a white solid, mp 82–84° C. 'H NMR (300 MHz, CDCl,) δ7.276 (d, J=9.0 Hz, 1H, ArH), 7.357 (d, J=8.1 Hz, 2H, ArH), 7.459 (m, 2H, ArH), 7.617 (t, 2H, ArH), 7.732 (m, 5H, ArH), 8.120 (m, TH, ArH), 8.206 (m, 3H, ArH), 8.903 (d, J=2.1 Hz, 1H, ArH), 11.254 (s, 1H, OH, $D_2O$ exchangeable) IR (KBr) v 1652.9, 1566.1, 1199.65 cm$^{-1}$.

Synthesis of 2—Hydroxy-5-(naphthalene-1-carbonyl)-N-phenyl-benzamide

Hydrogen chloride gas was slowly bubbled into a solution of 300 mg of aniline in 5 mL of isopropyl ether until the solution was saturated with hydrogen chloride. The resulting white precipitate of aniline hydrochloride salt was collected and dried. 0.0501 g of this salt, together with 1.50 g, (4.07 mmole) of the phenyl ester, described above, and 0.459 mL (5.04 mmole) of aniline, was placed in a 50 mL round bottom flask fitted with a distilling head connected with dry argon gas. The reaction mixture was first purged with dry argon gas for 30 minutes then the temperature was raised to 90° C. with an external oil bath to melt the ester. Finally, the temperature was raised to 170° C. and was maintained at 170° C. for 12 hours. During this period the TLC was checked several times to make sure the reaction was completed. Dry argon gas purge was used during the heating period.

Purity was checked by using TLC (silica gel plate) with 10:1 hexane and ethyl acetate. Four spots were observed on TLC, the target compound was the second spot from the bottom just a bit higher than aniline spot, and the color was light yellow.

Purification was achieved by using flash column chromatography on silica gel with 10:1 hexane to ethyl acetate solvent system. The product was collected and dried to give 0.398 g (27%) of light yellow solid, mp 100–104° C. 'H NMR (300 MHz, DMSO-$d_6$) δ6.846 (d, J=7.5 Hz, 2H, ArH), 6.910 (m, 2H, ArH), 7.139 (m, 3H, ArH), 7.262 (m, 2H, ArH), 7.492 (m, 3H, ArH), 7.640 (m, 2H, ArH), 7.725 (m, 3H, ArH), 8.057 (m, 2H, ArH), 8.441 (s, IH, ArH), 9.507 (s, 1H, OH, $D_2O$ exchangeable), 10.617 (s, 1H, NH, $D_2O$ exchangeable) IR (KBr) v 3059.8, 1642.2, 1593.1 cm$^{-1}$.

EXAMPLE 2

This embodiment demonstrates the effectiveness of the compounds of the present invention against gram positive bacteria. The MIC's for the compounds were determined by a modified microdilution tube dilution method described in "Methods for Dilution Antimicrobial Susceptibility Tests for Bacteria that Grow Aerobically" (National Committee for Clinical Laboratory Standards Approved Standards, 1997, NCCLS document M7-A4). In general the modifications were made because of the unique growth requirements for the fastidious oral organisms and for those bacteria that require anaerobic conditions. Reference is also made to "Methods for Antimicrobial Susceptibility of Anaerobic Bacteria" (National Committee for Clinical Laboratory Standards Approved Standards, 1997, NCCLS document M11-A4).

Briefly, the methods were as follows. Cultures were grown for 18–24hrs (aerobic bacteria) or 48–72 hrs (anaerobic bacteria) in the appropriate medium. For aerobic bacteria full strength brain heart infusion medium (BHI, Difco) was used. For anaerobic bacteria, half strength BHI (18.5 g/L) was supplemented by adding yeast extract (10 g/L), hemin (0.29 mL of a stock solution containing 0.1 g/200 mL d$H_2O$) and menadione (15 mL of a stock solution containing 0.15 mL in 30 mL 95% EtOH) was used. Initial cultures were diluted to approximately 1×10$^8$ CFU/mL for use as an inoculum. Each assay received 10 μL of the inoculum. The drugs were prepared from a stock solution contained in dimethyl sulfoxide (DMSO) and diluted into the culture medium. Final concentrations of the drugs ranged from 50 to 0.05 μg/assay. The tests were run in duplicate and were incubated appropriately with regard to oxygen requirements for 24 to 48 hrs as required. Anaerobic incubation was an atmosphere of 5% $CO_2$, 10% $H_2$, with the balance $N_2$. The lowest concentration of an antimicrobial agent at which no visible growth is noted was referred to as the MIC.

The compounds of the present invention used in this example NA1mF, NA1mC, NA2mF, NA2mC, NA1pC, NA1, NA1NpC, NA1pBz, NA1OHmF, NA1_3BnOPh, NA1mOPh and NA1mF2 have been described above. NA1pBz is a naphthylsalicylanilide of Formula 110 wherein Z is benzoyl at the para position. NA1mOPh has the structure of Formula 110 wherein Z is phenoxy at the meta position and NA1-2mOMe has the structure of Formula 110 wherein Z is —$OCH_3$ at both the meta positions. The structure of TMF-12 is described in U.S. Pat. No. 6,117,859. BPAmF, BPAmC and BBAmF are substituted or unsubstituted alkylsalicylanilides described in U.S. Pat. No. 4,287, 191. Their structures are also provided below.

BPAmF has the following structure:

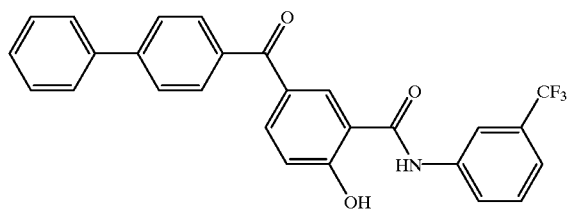

BPAmC has the following structure:

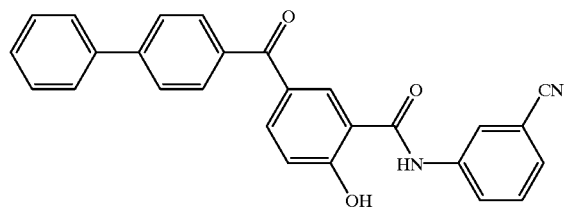

BBAmF has the following structure:

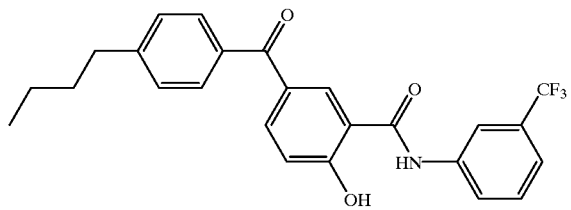

In Tables 1–5, NE indicates that the drug was not effective at a concentration >50 micrograms/ml and "–" indicates that the drug was not tested.

TABLE 1

Gram Positive

| Drug Code | S. mutans | S. sanguis | S.saliv-arius | P. acnes 6922 | P. acnes 11828 |
|---|---|---|---|---|---|
| NA1mF | 0.8 | 0.8 | 3.1 | 0.2 | 0.4 |
| NA1mC | 3.1 | 6.3 | 50 | 6.3 | 6.3 |
| NA2mF | NE | 0.8 | 50 | 0.4 | 0.4 |
| NA2mC | 6.3 | 6.3 | 50 | 6.3 | 12.5 |
| NA2pC | 1.6 | 6.3 | 50 | 6.3 | 6.3 |
| BPAmF | NE | NE | NE | 0.2 | 0.4 |
| BPAmC | NE | NE | NE | 0.2 | 12.5 |
| BBAmF | NE | NE | NE | 0.2 | 0.8 |
| NA1 | 50 | NE | NE | 25 | NE |
| NA1NpC | NE | — | — | 0.4 | — |
| NA1pBz | NE | — | — | NE | — |
| NA1OHmF | 6.3 | — | — | 3.1 | — |
| NA1-2mOMe | NE | — | — | NE | — |
| NA1_3BnOP | NE | — | — | NE | — |
| NA1mOPh | NE | — | — | NE | — |
| NAmF2 | 1.6 | — | — | 0.4 | — |
| TMF-12 | NE | 12.5 | NE | 0.4 | 0.2 |

TABLE 2

Gram Positive

| Drug Code | A. viscosus | S. aureus | Lact 7496 | M. luteus |
|---|---|---|---|---|
| NA1mF | <0.1 | 1.6/3.1 | 0.4 | 0.8 |
| NA1mC | 3.2 | 6.3/12.5 | 3.1 | 3.1 |
| NA2mF | NE | NE | 1.6 | 0.8 |
| NA2mC | 1.6 | NE | 12.5 | 3.1 |
| NA2pC | 1.6 | 6.3 | 6.3 | 3.1 |
| BPAmF | NE | NE | 6.3 | 3.1 |
| BPAmC | NE | NE | 12.5 | 3.1 |
| BBAmF | NE | NE | 6.3 | 3.1 |
| NA1 | 3.1 | 50 | — | — |
| NA1NpC | 0.8 | NE | — | — |
| NA1pBZ | NE | NE | — | — |
| NA1OHmF | 0.8 | NE | — | — |
| NA1-2mOMe | NE | NE | — | — |
| NA1_3BnOP | 6.3 | NE | — | — |
| NA1mOPh | NE | NE | — | — |
| NAmF2 | 0.8 | NE | — | — |
| TMF-12 | 1.6 | NE | 3.1 | 0.8 |

EXAMPLE 3

This embodiment demonstrates that effectiveness of the compounds of the present invention against gram negative bacteria. The method used was the same as described in Example 1.

TABLE 3

Gram Negative

| Drug Code | Fuso. 25586 | Aa Y4 | P. ging 381 | Pg 53977 | B. frag-ilis |
|---|---|---|---|---|---|
| NA1mF | 3.1 | 3.1 | <0.1 | <0.1 | 3.1 |
| NA1mC | 2.5 | 6.3 | 0.4 | 0.8 | NE |
| NA2mF | NE | NE | <0.4 | <0.4 | NE |
| NA2mC | NE | NE | 0.8 | 0.8 | 3.1 |
| NA2pC | 12.5 | 6.3 | 0.4 | 0.4 | 3.1 |
| BPAmF | NE | NE | <0.4 | <0.4 | 50 |
| BPAmC | NE | NE | <0.4 | <0.4 | 50 |
| BBAmF | NE | NE | <0.4 | <0.4 | NE |
| NA1 | — | — | 1.6 | — | — |
| NA1NpC | — | — | 0.2 | — | — |
| NA1pBz | — | — | NE | — | — |
| NA1OHmF | — | — | 0.8 | — | — |
| NA1-2mOMe | — | — | NE | — | — |
| NA1_3BnOP | — | — | 3.1 | — | — |
| NA1mOPh | — | — | NE | — | — |
| NAmF2 | — | — | 0.2 | — | — |
| TMF-12 | NE | NE | 0.4 | 0.4 | NE |

TABLE 4

Gram negative

| Drug Code | S. pyo 51339 | S. pyo 49399 | S. pyo 19615 | Str. pn 6303 | Str. pn 6301 | Str. pn 6305 |
|---|---|---|---|---|---|---|
| NA1mF | 1.6 | 0.78 | 0.63 | 0.18 | 0.78 | 0.39 |
| NA1mC | 12.5 | 12.5 | 25 | 0.18 | 1.56 | 1.56 |
| NA2mF | 0.4 | 3.2 | NE | 0.18 | 0.78 | 1.56 |
| NA2mC | NE | NE | NE | 6.78 | 1.56 | 0.39 |
| NA2pC | 3.2 | 3.2 | NE | 0.18 | 0.78 | 0.78 |
| BPAmF | 6.3 | 6.3 | NE | 0.18 | 1.56 | 0.78 |
| BPAmC | NE | NE | NE | 0.18 | 0.78 | 0.78 |
| BBAmF | 6.3 | 6.3 | NE | 0.18 | 0.78 | 0.39 |
| NA1 | — | 12.5 | — | — | — | — |
| NA1NpC | — | 6.3 | — | — | — | — |
| NA1pBz | — | NE | — | — | — | — |
| NA1OHmF | — | 3.1 | — | — | — | — |
| NA1-2mOMe | — | NE | — | — | — | — |
| NA1_3BnOP | — | 50 | — | — | — | — |
| NA1mOPh | — | NE | — | — | — | — |
| NAmF2 | — | 1.6 | — | — | — | — |
| TMF-12 | 0.32 | 0.8 | 0.32 | 0.78 | 0.39 | 0.78 |

None of the drugs tested were found to be effective against Salmonella, E.coli, Sal.chsuis and Citrobacter even at concentrations greater than 50 micrograms/mL. NE denotes a lack of a detectable effect at 50 micrograms per ml.

EXAMPLE 4

This embodiment illustrates the efficacy of the compounds of the present invention against Streptococcus strains. One of the strains, Str.pn.R was obtained from the Children's Hospital in Buffalo (strain 00-041-0614). It was isolated from the bronchial wash and was found to be beta lactamase positive. The sensitivity of this strain was tested against several known antibiotics. The results indicated that it was sensitive to Clindamycin, Vancomycin, Trovoflox, Rifampin but resistant to penicillin and erythromycin. The efficacy, measured as MIC values, is shown in Table 5.

TABLE 5

Mean Streptococcus MIC values

| Drug Code | Str. pyo | Str. pn | Str. pn. R |
|---|---|---|---|
| NA1mF | 1.0 | 0.45 | 0.78 |
| NA1mC | 16.67 | 1.10 | 12.5 |
| NA2mF | — | 0.84 | 0.78 |
| NA2mC | NE | 0.91 | 6.25 |
| NA2pC | — | 0.58 | 3.12 |
| BPAmF | — | 0.84 | NE |
| BPAmC | — | 0.58 | NE |
| BBAmF | — | 0.45 | NE |
| TMF-12 | 0.47 | 0.65 | 0.78 |

EXAMPLE 5

This embodiment describes the sensitivity of various staphylococcus strains to the compounds of the present invention. The staphylococcus species R is a strain 00-045-1209 from the Children's Hospital in Buffalo. It was isolated from the peritoneal cavity (fluid culture) of an individual. It was coagulase negative. The sensitivity of this strain was tested agaisnt several known antibiotics. The results indicated that it was sensitive to vancomycin but resistant to amoxicillin, clindamycin, erythromycin, oxacillin, azithromycin, and cefotaxime. However, this strain was found to be sensitive to the compounds of the present invention with the highest effect being observed with NA1mF (Table 5).

The *S.aureus* R2 species is a strain 00-42-1066 from the Children's Hospital in Buffalo. It was isolated from a wound in an individual. It was coagulase negative. The sensitivity of this strain was tested agaisnt several known antibiotics. The results indicated that it was sensitive to vancomycin but resistant to amoxicillin, clindamycin, erythromycin, oxacillin, azithromycin, and cefotaxime.

TABLE 5

| Drug Code | S. aureus | S. species R | S. aureus R2 |
|---|---|---|---|
| NA1mF | 3.1 | 1.6 | 1.6 |
| NA1mC | 12.5 | 25.0 | 6.3 |
| NA2mF | NE | 25.0 | 25.0 |
| NA2mC | NE | NE | NE |
| NA2pC | 6.3 | 12.5 | NE |
| BPAmF | NE | NE | NE |
| BPAmC | NE | NE | NE |
| BBAmF | NE | NE | NE |
| TMF | NE | NE | NE |

EXAMPLE 6

This embodiment illustrates that the antiinflammatory effects of the compounds of the present invention is comparable to those of known antiinflammatory agents such as saliflor (TMF-12). For this illustration, the TPA mouse ear inflammation assay was used for acute inflammation as described in U.S. Pat. Nos. 5,958,911 and 6,117,859 (incorporated herein by reference). To quantitate inflammation, ear biopsies were weighed six hours after treatment with TPA (positive control) and the simultaneous application of a compound of the present invention (NA1mF, NA2mF), TMF-12 or in the absence of TPA (negative control). The results of the experiment are shown in FIG. 1.

Various embodiments are presented herein for illustrative purposes and are not to be construed as restrictive. Modifications of the embodiments presented herein that are obvious to those skilled in the art are intended to be within the scope of the invention and the claims.

We claim:

1. A compound having the formula

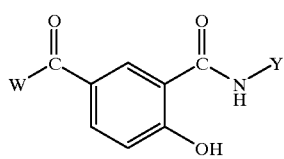

wherein W is a substituted or unsubstituted naphthyl ring, wherein the substitution on the naphthyl ring W consists of replacing one or more —H with a moiety selected from the group consisting of —OH, alkyl containing 1–6 carbon atoms, O-alkyl containing 1–6 carbon atoms, branched alkyl containing 1–6 carbon atoms, cycloalkyl containing 1–6 carbon atoms and combinations thereof, wherein Y is selected from the group consisting of substituted or unsubstituted phenyl and substituted or unsubstituted naphthyl, wherein the substitution on the phenyl or naphthyl ring Y consists of replacing one or more —H with a moiety selected from the group consisting of cyano, trifluoromethyl, nitro, methoxy, phenoxy, benzoyl, phenoxymethyl and combinations thereof.

2. The compound of claim 1 having the following structure.

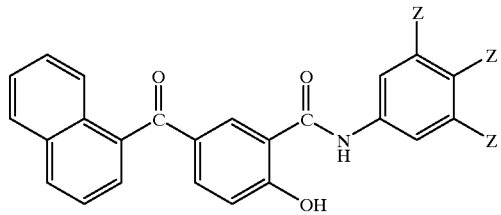

wherein Z is independently at each position selected from the group consisting of —H, —CF$_3$, —CN, —NO$_2$ methoxy, phenoxy, benzoyl and phenoxymethyl; or an isomer thereof.

3. The compound of claim 2, wherein Z is —CF$_3$ at the meta or para position.

4. The compound of claim 2, wherein Z is —CN at the meta or para position.

5. The compound of claim 2, wherein Z is —NO$_2$ at the meta or para position.

6. The compound of claim 2, wherein Z is a methoxy group at the para or meta position.

7. The compound of claim 2, wherein Z is phenoxy group at the meta or para position.

8. The compound of claim 2, wherein Z is benzoyl group at the meta or para position.

9. The compound of claim 2, wherein z is phenoxymethyl at the meta or para position.

10. The compound of claim 2, wherein Z is CF$_3$ at both the meta positions.

11. The compound of claim 1, having the following structure

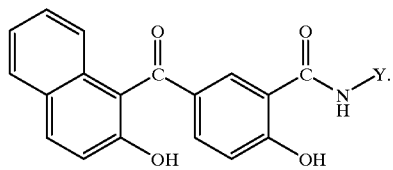

12. The compound of claim 1 having the following structure

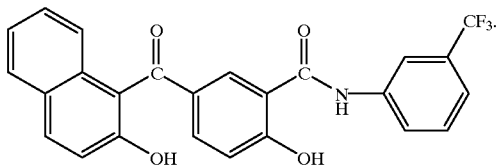

13. The compound of claim 1 having the following structure

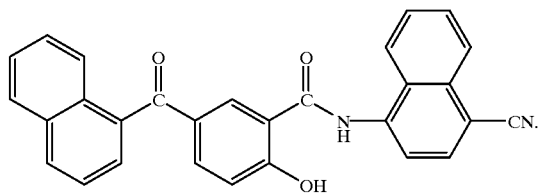

14. A method of treating a bacterial infection in an individual comprising contacting the infected area with a therapeutically effective amount of a compound of the following structure

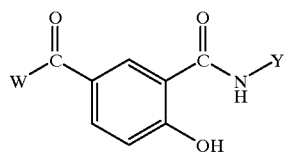

wherein W is a substituted or unsubstituted naphthyl ring, wherein the substitution on the naphthyl ring W consists of replacing one or more —H with —OH, wherein Y is selected from the group consisting of substituted or unsubstituted phenyl and substituted or unsubstituted naphthyl, wherein the substitution on the phenyl or naphthyl ring Y consists of replacing one or more —H with a moiety selected from the group consisting of cyano, trifluoromethyl, nitro, phenoxymethyl and combinations thereof.

15. The method of claim 14, wherein the compound has following structure

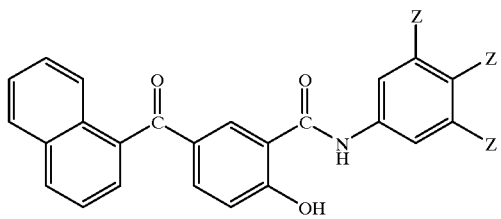

or an isomer thereof.

16. The method of claim 15, wherein Z is —CN at the meta or para position.

17. The method of claim 15, wherein Z is —NO₂ at the meta or para position.

18. The method of claim 15, wherein Z is —CF₃ at the meta or para position.

19. The method of claim 15, wherein Z is phenoxymethyl at the meta or para position.

20. The method of claim 14, wherein the compound has the following structure

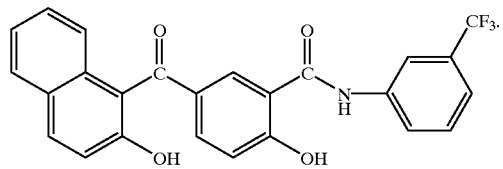

21. The method of claim 14, wherein the compound has the following structure

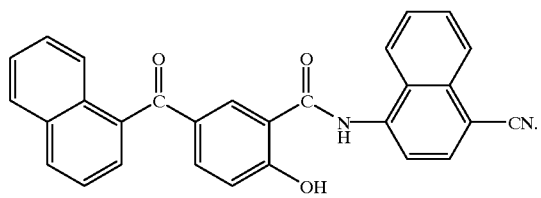

22. The method of claim 14, wherein the compound has the following structure

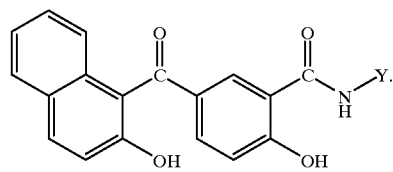

23. The method of claim 14, wherein the bacterial infection is caused by organisms selected from the group consisting of gram positive bacteria, gram negative bacteria and combinations thereof.

24. The method of claim 23, wherein the gram positive bacteria are selected from the group consisting of *S. mutans, S.sanguis, S.salivarius, P.acnes, A.viscosus, S.aureus, L. rhamnosus*.

25. The method of claim 23, wherein the gram negative bacteria are selected from the group consisting of *Sal. chsuis, Fuso. nucleatum, A. actinomycetemcomitans, E. coli, P.gingivalis, B. fragilis* and Citrobacter.

26. A method of treating inflammation in an individual comprising contacting the affected area with an amount sufficient to ameliorate the inflammatory condition, of a compound of the following formula:

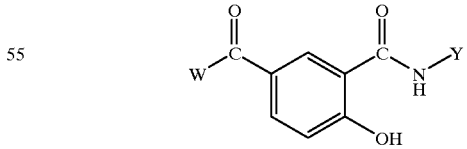

wherein W is a substituted or unsubstituted naphthyl ring, wherein the substitution on the naphthyl ring W consists of replacing one or more —H with a moiety selected from the group consisting of —OH, alkyl containing 1–6 carbon atoms, O-alkyl containing 1–6 carbon atoms, branched alkyl containing 1–6 carbon atoms, cycloalkyl containing 1–6 carbon atoms and combinations thereof, wherein Y is selected from the group consisting of substituted or unsubstituted phenyl and substituted or unsubstituted naphthyl, wherein the substitution on the phenyl or naphthyl ring Y consists of replacing one or more —H with a moiety selected from the group consisting of cyano, trifluoromethyl, nitro, methoxy, phenoxy, benzoyl, phenoxymethyl and combinations thereof.

27. The method of claim 26, wherein the compound has the following formula:

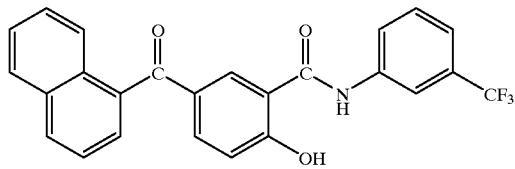

or an isomer thereof.

* * * * *